(12) United States Patent
Knobel et al.

(10) Patent No.: US 12,157,881 B2
(45) Date of Patent: Dec. 3, 2024

(54) USE OF A DEFOAMER FOR MAINTAINING DISPERSED MORPHOLOGY IN SUBMERGED FUNGAL FERMENTATION

(71) Applicant: The Protein Brewery B.V., Breda (NL)

(72) Inventors: Kirsten Knobel, Rotterdam (NL); Ap De Haan, Prinsenbeek (NL); Wilhelmus Theodorus Antonius Maria De Laat, Breda (NL)

(73) Assignee: The Protein Brewery B.V., Breda (NL)

( * ) Notice: Subject to any disclaimer, the term of this patent is extended or adjusted under 35 U.S.C. 154(b) by 0 days.

(21) Appl. No.: 17/793,942

(22) PCT Filed: Jan. 22, 2021

(86) PCT No.: PCT/EP2021/051433
§ 371 (c)(1),
(2) Date: Jul. 20, 2022

(87) PCT Pub. No.: WO2021/148592
PCT Pub. Date: Jul. 29, 2021

(65) Prior Publication Data
US 2023/0046934 A1     Feb. 16, 2023

(30) Foreign Application Priority Data
Jan. 23, 2020  (EP) .................................. 20153414

(51) Int. Cl.
*C12N 1/14*   (2006.01)
*A23J 1/00*   (2006.01)
*A23J 3/20*   (2006.01)
*C12N 1/38*   (2006.01)

(52) U.S. Cl.
CPC .............. *C12N 1/145* (2021.05); *A23J 1/008* (2013.01); *A23J 3/20* (2013.01); *C12N 1/38* (2013.01); *C12N 2500/60* (2013.01)

(58) Field of Classification Search
CPC ...... C12N 1/145; C12N 1/38; C12N 2500/60; C12N 1/14; A23J 1/008; A23J 3/20; C12R 2001/845; C12P 21/00
See application file for complete search history.

(56) References Cited

U.S. PATENT DOCUMENTS

2014/0342396 A1* 11/2014 De Laat .................. C12P 35/00
                                                     435/134

FOREIGN PATENT DOCUMENTS

WO   WO2012/122613 A1   9/2012
WO   WO2018029353 A1    2/2018

OTHER PUBLICATIONS

Drop (Unit) defined by Wikipedia, retrieved on Oct. 17, 2023, 2 pages of PDF. (Year: 2023).*

J. van der Veen, Ph.D. thesis "Production of single cell protein by cultivation of yeasts on fats and fat products", 1974, 146 pages. (Year: 1974).*
El Enshasy, Hesham. (2007). Filamentous Fungal Cultures-Process Characteristics, Products, and Applications. In Bioprocessing for value-added products from renewable resources. Bioprocessing for Value-Added Products from Renewable Resources Shang-Tian Yang (Editor), p. 225-261. (Year: 2007).*
Papagianni et al., Biotechnology Advances, (2004), vol. 22, p. 189-259. (Year: 2004).*
A E Reade et al: "High-Temperature Production of Protein-Enriched Feed from Cassava by Fungi", Applied Microbiology, vol. 30, No. 6, Dec. 1, 1975, pp. 897-904.
Coleen A. Stevens et al: "Production of Microbial Biomass Protein from Potato Processing Wastes by Cephalosporium eichhorniae", Applied and Environmental Microbiology, vol. 53, No. 2, Feb. 1, 1987, pp. 284-291.
Junker Beth: "Foam and its mitigation in fermentation Systems", Biotechnology Progress, American Chemical Society, vol. 23, No. 4, Jan. 1, 2007, pp. 767-784.
Cormac O' Cléirigh: "Quanti Fication and Regulation of Pellet Morphology in Streptomyces Hygroscopicus Var. Geldanus Cultures", Thesis, School of Biotechnology, Dublin City University, Jul. 1, 2005, pp. 1-222.
Suman, Gour, et al. "Single cell protein production: a review." International Journal of Current Microbiology and Applied Sciences 4.9 (2015): 251-262.
Bajpai, Pratima, and Pramod K. Bajpai. "Single cell protein production from rayon pulp will waste by Paecilomyces variotii." Journal of Fermentation Technology 65.3 (1987): 349-351.
Grajek, W. "Production of protein by thermophilic fungi from sugar-beet pulp in solid-state fermentation." Biotechnology and bioengineering 32.2 (1988): 255-260.
Grajek, W. "Cooling aspects of solid-state cultures of mesophilic and thermophilic fungi." Journal of Fermentation Technology 66.6 (1988): 675-679.
Junker, B. H., et al. "Early phase process scale-up challenges for fungal and filamentous bacterial cultures." Applied biochemistry and biotechnology 119.3 (2004): 241-277.
Veiter, Lukas, Vignesh Rajamanickam, and Christoph Herwig. "The filamentous fungal pellet—relationship between morphology and productivity." Applied Microbiology and Biotechnology 102 (2018): 2997-3006.

* cited by examiner

*Primary Examiner* — Kade Ariani
(74) *Attorney, Agent, or Firm* — N.V. Nederlandsch Octrooibureau

(57) ABSTRACT

The present invention relates to the use of a defoaming agent for preventing pellet morphology of thermophilic fungi when grown at acidic pH in chemically defined media. The invention pertains to processes for producing a fermentation product, wherein the thermophilic fungus, e.g. a *Rhizomucor* species, is grown in submerged culture at acidic pH in a chemically defined medium and wherein the strain is cultured in the presence of a defoaming agent. The defoaming agent can be a vegetable oil such as olive or sun flower oil and the fermentation product can be single cell protein in the form of biomass of the thermophilic fungus for use as a dietary source of protein.

13 Claims, 1 Drawing Sheet

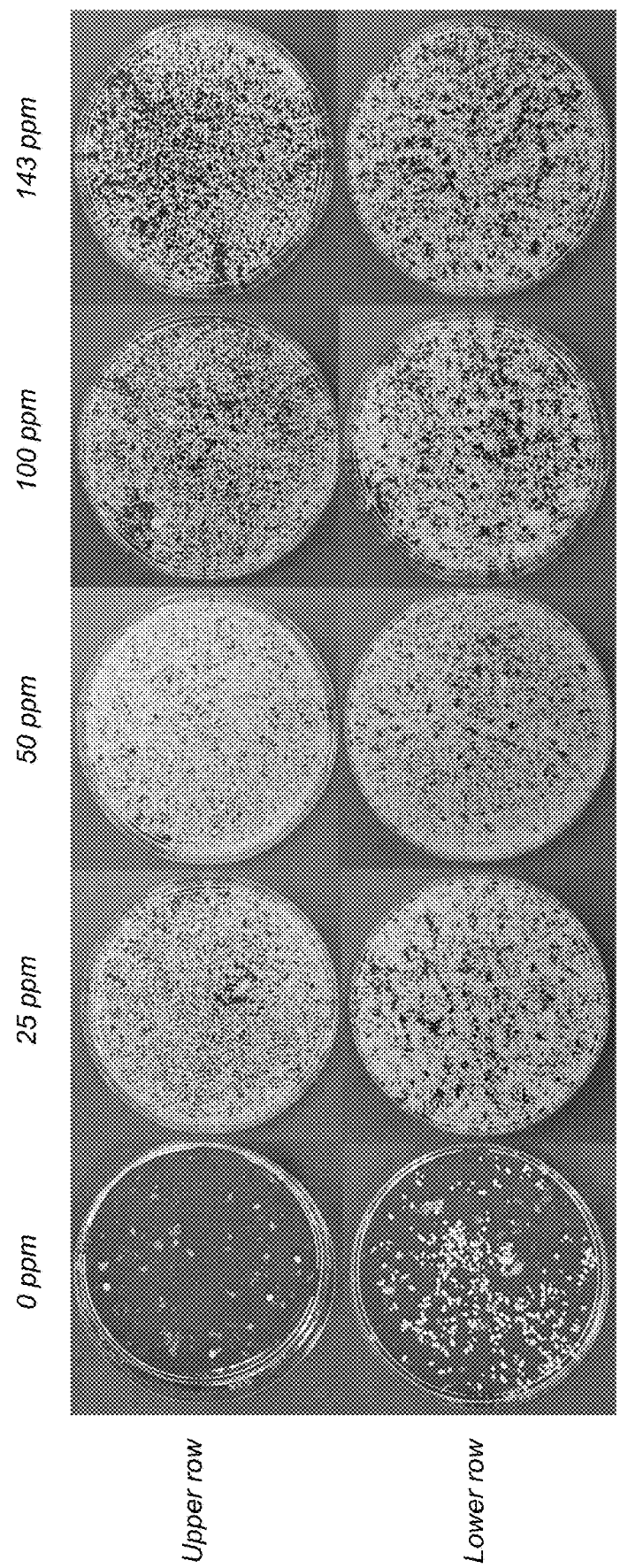

USE OF A DEFOAMER FOR MAINTAINING DISPERSED MORPHOLOGY IN SUBMERGED FUNGAL FERMENTATION

FIELD OF THE INVENTION

The present invention relates to the fields of microbiology and fermentation technology. In particular, the invention relates to the production of single cell protein for use in food products and animal feed, through fermentation of thermophilic fungi.

BACKGROUND OF THE INVENTION

The increasing global population leads to a soaring demand for proteins that can no longer be sustained by the conventional ways of producing protein-rich food such meat, dairy products and fish. More sustainably ways of producing protein for human consumption are urgently required to deliver on sustainability, health and economy.

One method for producing a dietary source of protein for human food or animal feed is to produce "single cell protein" (SCP) by means of fermentation (Suman et al., 2015, Int J. Curr. Microbiol. Appl. Sci., Vol 4, No 9, pp 251-262). Fermentation in this respect is understood as the microbial conversion of carbon-rich feedstocks into protein-rich products consisting of microbial cells such as bacteria, yeasts or fungi. The use of SCP as animal feed and food ingredient brings the further advantages that microbial cells have a high content of essential amino acids. Furthermore, in particular fungal cells can be very rich in trace elements and vitamins making the fermented feedstuffs very nutritive.

Quorn™, is a mycoprotein produced as SCP by fermentation of the fungus *Fusarium venenatum* and contains Vitamin B1 (Thiamin), Vitamin B2 (Riboflavin), Vitamin B3 (Niacin), Vitamin B5 (Pantothenic acid) and Biotin (www.mycoprotein.org).

One problem in SCP production is the concentration of the SCP-biomass that is produced in diluted fermentation broth. Another problem is that in order to avoid infection when using mesophilic microorganisms for SCP production, sterile fermentation conditions need be applied, which leads to prohibitive operational costs due to high capital investments and energy demands (Bajpai and Bajpai, 1987, J. Ferment. Technol. 65, 3: 349-351). Some of these issues have been addressed by using solid state fermentation with thermophilic fungi (Grajek, 1987, Biotechnol. Bioengineer. 32: 255-260; and Grajek, 1988, J. Ferment. Technol. 66, 6: 675-679). However, scaling up of such solid state processes poses problems with aeration and cooling.

WO2018/029353A1 addresses these problems by producing single cell protein from thermophilic fungi in a process wherein the fungi can be grown under non-sterile conditions in submerged culture by applying a combination of acidic pH (to prevent bacterial growth) and high temperature (to prevent growth of yeasts). WO2018/029353A1 screens several species of thermophilic fungi for their suitability in such a process for producing SCP and identifies *Rhizomucor* species as thermophilic fungi that combine the favourable properties of good growth at high temperature and acidic pH with a sievable morphology and a high protein content.

In submerged culture, fungi can either grow in dispersed form or as spherical pellets consisting of lobular aggregated hyphal structures. Junker et al. (Appl Biochem Biotechnol. 2004; 119:241-78) and Veiter et al. (Appl Microbiol Biotechnol. 2018; 102:2997-3006) describe that pellet formation depends on many different factors and significantly varies between species. These authors also review a large variety measures to alter the fungal morphology, such as rates of agitation and/or aeration, pH, presence of divalent cation such as manganese, spore inoculum size or volume, addition of surfactant (Tween 20 or 80), anionic polymers, microparticles ($Al_2O_3$), etc.

There is however still a need for further optimisation of fermentation processes wherein thermophilic fungi are applied to produce fermentation products such as SCP. It is an object of the present invention to provide improved processes for the fermentation of thermophilic fungi as well as products obtained in such processes.

SUMMARY OF THE INVENTION

In a first aspect, the present invention pertains to a process for producing a fermentation product, wherein preferably, the process comprises the steps of: a) growing a strain of a thermophilic fungus in submerged culture in a chemically defined medium, at a pH of less than 5.0, whereby the strain converts nutrients in the medium to the fermentation product and wherein preferably the strain is cultured in the presence of a defoaming agent, more preferably a food-grade defoaming agent; and, b) optionally, recovery of the fermentation product produced in step a). Preferably, in the process, the defoaming agent is at least one of an oil-based defoamer, a polyalkylene glycol-based defoamer and a silicon-based defoamer. More preferably, the defoaming agent comprises a vegetable oil, preferably an edible vegetable oil. Most preferably, the vegetable oil is selected from the group consisting of canola (rapeseed) oil, coconut oil, corn oil, cottonseed oil, olive oil, palm oil, palm kernel oil, linseed oil, peanut oil, safflower oil, soya bean oil, sunflower oil and high-oleic sunflower oil, of which olive oil or high-oleic sunflower oil are preferred.

In one embodiment of the process of the invention, the defoaming agent preferably is present and maintained in the chemically defined medium at a concentration of at least 1 ppm (w/v).

In one embodiment of the process of the invention, the fungal strain preferably is a strain of a fungal genus selected from the group consisting of *Rasamsonia, Talaromyces, Penicillium, Acremonium, Humicola, Paecilomyces, Chaetomium, Rhizomucor, Rhizopus, Thermomyces, Myceliophthora, Thermoascus, Thielavia, Mucor, Stibella, Melanocarpus, Malbranchea, Dactylomyces, Canariomyces, Scytalidium, Myriococcum, Corynascus,* and *Coonemeria,* of which the genus *Rhizomucor* is preferred. More preferably, the fungal strain is of the species *Rhizomucor pusillus*, most preferably the strain is *Rhizomucor pusillus* strain CBS 143028, or a strain that is a single colony isolate and/or a derivative of strain CBS 143028.

In one embodiment of the process of the invention, the carbon source in the chemically defined medium preferably consist of at least one of a hydrophilic carbon source and the defoaming agent, wherein preferably the hydrophilic carbon source consists of carbohydrate or an organic acid, and wherein more preferably the defoaming agent is a vegetable oil.

In one embodiment of the process of the invention, preferably step a) of the process, is carried out as is a fed-batch process, a repeated fed-batch process or a continuous process, more preferably a carbon-limited process.

In one embodiment of the process of the invention, the fermentation product preferably is single cell protein in the form of biomass of thermophilic fungus, wherein the process optionally comprises a step b) of recovery of SCP from the medium in the form of biomass of the thermophilic fungus grown in step a). Preferably, the biomass is recovered from the medium by at least one of sieving, filtration and decantation, whereby preferably the dry matter concentration of the sieved, filtered or devastated biomass (cake) is at least 12% (w/v), and wherein more preferably, the biomass cake is further dried by pressing residual water out.

In one embodiment of the process of the invention, the biomass cake preferably is milled and further dried to a biomass powder by warm air, by freeze drying, preferably under vacuum, or by flash drying, drum drying or by using a paddle dryer under vacuum, preferably to a water content of no more than 5% (w/w).

In a second aspect the invention relates to an SCP product comprising biomass of a thermophilic fungal strain as defined in the first aspect of the invention, wherein preferably at least one of: a) the biomass is obtainable in process of the invention; and, b) the biomass comprises at least 1 ppm (w/v) of a defoaming agent as here defined in the first aspect of the invention. Preferably, the SCP product comprises biomass cake with dry matter concentration of at least 12% (w/v), or a biomass powder with a water content of no more than 5% (w/w/).

In a third aspect, the invention relates to a food or beverage product, a pet food product or animal feed comprising an SCP product as defined in the second aspect of the invention.

In a fourth aspect, the invention pertains to a use of a defoaming agent as here defined in the first aspect of the invention, for at least one of: i) preventing pellet morphology; ii) inducing dispersed morphology; and iii) maintaining dispersed morphology; of a strain of thermophilic fungus as defined in the first aspect of the invention, when grown at a pH of less than 5.0 in a chemically defined medium.

DESCRIPTION OF THE INVENTION

Definitions

Unless defined otherwise, technical and scientific terms used herein have the same meaning as commonly understood by one of ordinary skill in the art to which this disclosure belongs. One skilled in the art will recognize many methods and materials similar or equivalent to those described herein, which could be used in the practice of the present invention. Indeed, the present invention is in no way limited to the method.

For purposes of the present invention, the following terms are defined below.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "and/or" indicates that one or more of the stated cases may occur, alone or in combination with at least one of the stated cases, up to with all of the stated cases.

As used herein, with "At least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

The word "about" or "approximately" when used in association with a numerical value (e.g. about 10) preferably means that the value may be the given value (of 10) more or less 0.1% of the value.

The term "single cell protein" will be abbreviated "SCP" and is herein understood to refers to biomass consisting essentially of cells of organisms that exist in unicellular, or single cell, state, including unicellular bacteria, yeasts, fungi or algae, and which biomass, preferably in dried form, is suitable as dietary source of protein or protein supplement in human food or animal feed.

"Fungi" are herein defined as eukaryotic microorganisms and include all species of the subdivision Eumycotina (Alexopoulos et al., 1962, In: Introductory Mycology, John Wiley & Sons, Inc., New York). The term fungus thus includes both filamentous fungi and yeast. "Filamentous fungi" are herein defined as eukaryotic microorganisms that include all filamentous forms of the subdivision Eumycotina and Oomycota (as defined by Hawksworth et al., 1983, In: Ainsworth and Brisby's Dictionary of the Fungi. $7^{th}$ ed. Commonwealth Mycological Institute, Kew, Surrey). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. A thermophilic fungus for use in the invention is a fungus that grows at a temperature of at least 45° C., sometimes even higher than 56° C.

The term "fermentation" or "fermentation process" is herein broadly defined in accordance with its common definition as used in industry as any (large-scale) microbial process occurring in the presence or absence of oxygen, comprising the cultivation of at least one microorganism whereby preferably the microorganism produces a useful product at the expense of consuming one or more organic substrates. The term "fermentation" is herein thus has a much broader definition than the more strict scientific definition wherein it is defined as being limited a microbial process wherein the microorganism extracts energy from carbohydrates in the absence of oxygen. Likewise, the term "fermentation product" is herein broadly defined as any useful product produced in a (large-scale) microbial process occurring in the presence or absence of oxygen.

Detailed Description of the Invention

The inventors found that while thermophilic fungi such as of *Rhizomucor pusillus* can be grown at low pH on media with complex carbon sources such as potatoes, fermentations of these fungi at low pH on a chemically defined medium using glucose as carbon source were found to prematurely terminate due to pellet formation. In submerged culture, fungi can either grow in dispersed form or as spherical pellets consisting of lobular aggregated hyphal structures. It is known that fungi may have problems growing at low pH, due to morphological changes from disperse mycelium to pellets. It has been suggested that the assimilation plays nutritional and morphogenetic roles in the development of thermophilic fungi (Maheshwari et al. 2000, Microbiol Mol Biol Rev; 64(3):461-488). This theory is based on the observation that low pH reduces the solubility of $CO_2$ limiting its availability for assimilation by the anaplerotic enzyme pyruvate carboxylase (Gupta and Maheshwari, 1985, Arch Microbiol, 141:164-169). Similarly, when the fungus grows in the form of pellets, diffusion of nutrients to the inside of the pellet will be restricted, which can be prohibitive to fungal growth as seen with the thermophilic fungi when grown at low pH on a chemically defined medium. Dispersed fungal morphology is desirable as it allows the fungus to grow faster due to having less diffusion limitation as compared to pellets. Junker et al. (Appl Biochem Biotechnol. 2004, 119:241-78) and Veiter et al. (Appl Microbiol Biotechnol. 2018, 102:2997-3006) describe that pellet formation depends on many different factors and significantly varies between species. The inventors have now surprisingly found that pellet formation in thermophilic fungi such as of *Rhizomucor pusillus* when grown can be at low pH on a chemically defined medium can be effectively prevented by inclusion of a defoamer in the fermentation medium.

In a first aspect, the invention therefore relates to a process for producing a fermentation product, wherein the process comprises the steps of: a) growing a strain of a thermophilic fungus in a chemically defined medium, at a pH of less than 5.0, whereby the strain converts nutrients in the medium to the fermentation product and wherein the strain is cultured in the presence of a defoaming agent; and, b) optionally, recovery of the fermentation product produced in step a). Preferably in step a) the fungal strain is grown in submerged culture.

Defoaming agents are generally well-known in the art (see e.g. en.wikipedia.org/wiki/Defoamer). A defoaming agent is a chemical additive that reduces and hinders the formation of foam in industrial process liquids, such as fermentation broths. While strictly speaking, defoamers eliminate existing foam and anti-foamers prevent the formation of further foam, the terms defoaming agent, anti-foam agent and defoamer are herein used interchangeably.

Generally, a defoamer is insoluble in the foaming medium and has surface active properties. A defoaming agent for use in the chemically defined aqueous culture media of the invention will therefore usually have a hydrophobic character, i.e. comprising or consisting of hydrophobic molecules. Furthermore, a defoaming agent for use in a processes of the invention preferably is compatible with a fermentation process in the sense that the agent is not toxic to the thermophilic fungus or otherwise negatively impacts its growth and preferably does not interact with medium component in a way that negatively impacts the process or the fermentation products produced thereby. Defoaming agents that are suitable for application in fermentation processes are generally well known in the art. A defoaming agent that is suitable for use in fermentation processes of the invention preferably is at least one of an oil-based defoamer, a polyalkylene glycol-based defoamer and a silicon-based defoamer. Examples thereof include respectively vegetable or mineral oils and animal fat, polypropylene glycol (PPG) or polyethylene glycol (PEG), Antifoam C1OOK (Basildon Chem. Comp. Ltd, Abingdon, Oxford, UK) and Struktol® SB 420 (Schill+Seilacher "Struktol" GmbH, Hamburg, Germany).

The choice of a defoaming agent for use in processes of the invention will depend on the application of the fermentation product that is produced in the process. In some embodiments, the fermentation product is to be applied in products for human or animal consumption, e.g. as SCP in the form of biomass of thermophilic fungus obtained in a process of the invention. In such instances the defoaming agent preferably is a food-grade defoaming agent. A preferred food-grade defoaming agent is a clean-label defoaming agent.

A preferred defoaming agent for use in a process of the invention comprises or consist of a vegetable oil, preferably an edible vegetable oil. A preferred (edible) vegetable oil for use as defoaming agent in a process of the invention is an oil is selected from the group consisting of canola (rapeseed) oil, coconut oil, corn oil, cottonseed oil, olive oil, palm oil, palm kernel oil, linseed oil, peanut oil, safflower oil, soya bean oil, sunflower oil and high-oleic sunflower oil.

In order to prevent oxidative deterioration of the organoleptic properties (e.g. rancidity) of the fermentation product produced in a process of the invention, e.g. SCP, the vegetable oil used as defoaming agent preferably has a reduced content of unsaturated fatty acids. Preferably the vegetable oil at least has a reduced content of polyunsaturated fatty acids, e.g. no more than 20, 18, 15, 12, 10, 8 or 5% of polyunsaturated fatty acids.

It is further preferred for ease of manipulation that the oil is liquid at room temperature.

A preferred vegetable oil for use as defoaming agent in a process of the invention is therefore olive oil or high-oleic sunflower oil, of which olive oil is most preferred.

Only a small amount of the defoaming agent needs to be present during the culturing of the fungal strain in step a) of the process of the invention to maintain the dispersed morphology of the fungal strain, which supports good growth. Preferably, the defoaming agent is present and/or is maintained in the chemically defined medium at a concentration of at least 1, 2, 5, 10, 25, 50, 75, 100, 125 or 135 ppm (w/v). It is understood that in order to maintain a minimum concentration, the defoaming agent may be fed during step a) of the process of the invention, as a result of the agent being consumed by the growing fungal strain or being diluted in case of a fed-batch or continuous type of process. On the other hand, the concentration the defoaming agent in the chemically defined medium need not exceed 150, 200, 400, 800, 1200 ppm (w/v), although higher concentrations are not excluded from the invention. The antifoaming agent can be added either continuously, or by demand, e.g. triggered by a defoaming sensor or a capacitive sensor, or the antifoaming agent can be added by intermittent feeding. The feed rate of the defoaming agent can be optimized in many aspects and even mixtures of defoaming agents can be used as improved or more cost effective options.

In one embodiment of the invention, step a) of the process preferably comprises that the fungus is grown in submerged culture.

In one embodiment of the invention, in step a) the fungus is preferably grown under non-sterile conditions.

In one embodiment of the invention, in step a) the fungus is preferably grown at a temperature of 30, 31, 32, 33, 34, 35, 36, 37, 38, 39, 40, 41, 42, 43, 44, 45, 46, 47, 48, 49, 50, 51, 52, 53, 54 or 55° C. or more.

In one embodiment of the invention, in step a) the fungus is preferably grown at a pH less than 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6 or 2.5.

A thermophilic fungus for use in the invention preferably is filamentous fungus. A preferred thermophilic fungus for use in the invention is a strain of a fungal genus selected from the group consisting of *Rasamsonia, Talaromyces, Penicillium, Acremonium, Humicola, Paecilomyces, Chaetomium, Rhizomucor, Rhizopus, Thermomyces, Myceliophthora, Thermoascus, Thielavia, Mucor, Stibella, Melanocarpus, Malbranchea, Dactylomyces, Canariomyces, Scytalidium, Myriococcum, Corynascus,* and *Coonemeria.* More preferably, the thermophilic fungus is a strain of a fungal species selected from the group consisting of *Rasamsonia composticola, Talaromyces emersonii, Rhizomucor miehei, Rhizomucor pusillus, Thermomucor indica-seudaticae, Thielava terricola, Thielava terrestris, Thermoascus*

*thermophilus* of which the strains *Rasamsonia composticola* CBS 141695, *Thermomucor indicae-seudaticae* CBS143027, *Rhizomucor miehei* CBS143029, *Rhizomucor pusillus* CBS 143028, *Thermascus thermophilus* CBS 528.71 and *Thielavia terrestris* CBS 546.86 are preferred.

In a preferred embodiment, the thermophilic fungus is a strain of the Class Zygomycete, of which the Family Mucoraceae is preferred. More preferably the thermophilic fungus is a strain of a genus selected from the genera *Mucor, Rhizomucor* and *Rhizopus*, of which the genus *Rhizomucor* is preferred. Most preferably the thermophilic fungus is a strain of a species selected from the species *R. endophyticus, R. miehei, R. pakistanicus, R. tauricus, R. variabilis* and *R. pusillus*, of which the species *Rhizomucor pusillus* is preferred.

Preferred strains of the above-mentioned thermophilic fungi for use in the invention include the following strains that were deposited under the regulations of the Budapest Treaty at the Westerdijk Fungal Biodiversity Institute Utrecht, The Netherlands (formerly referred to as Centraalbureau voor Schimmelcultures, CBS) *Rhizomucor pusillus* CBS 143028, *Rhizomucor miehei* CBS 143029 and *Rhizopus* sp. CBS 143160, of which *Rhizomucor pusillus* CBS 143028 is most preferred.

In one embodiment of a process of the invention, the strain of a thermophilic fungus is preferably grown or cultured in a chemically defined medium. The term "chemically defined" is understood to be used for fermentation media which are essentially composed of chemically defined constituents, i.e. the chemical composition of essentially all the chemicals used in the media is known. A fermentation medium which is essentially composed of chemically defined constituents includes a medium which does not contain a complex carbon and/or nitrogen source, i.e. which does of contain complex raw materials having a chemically undefined composition. The chemically defined media preferably do not comprise of chemically ill-defined yeast, animal or plant tissues; they do not comprise peptones, extracts or digests or other components which may contribute chemically poorly defined proteins and/or peptides and/or hydrolysates to the media. Chemically undefined or poorly defined chemical components are those whose chemical composition and structure is not well known, are present in poorly defined and varying composition or could only be defined with enormous experimental effort.

Nonetheless, a fermentation medium which is essentially composed of chemically defined constituents may however further include a medium which comprises an essentially small amount of a complex nitrogen and/or carbon source, an amount as defined below, which typically is not sufficient to maintain growth of the microorganism and/or to guarantee formation of a sufficient amount of biomass.

In that regard, complex raw materials have a chemically undefined composition due to the fact that, for instance, these raw materials contain many different compounds, among which complex heteropolymeric compounds, and have a variable composition due to seasonal variation and differences in geographical origin. Typical examples of complex raw materials functioning as a complex carbon and/or nitrogen source in fermentation are soybean meal, cotton seed meal, corn steep liquor, yeast extract, casein hydrolysate, molasses, and the like.

An essentially small amount of a complex carbon and/or nitrogen source may be present in the chemically defined medium of the invention, e.g. as carry-over from the inoculum for the main fermentation. The inoculum for the main fermentation is not necessarily obtained by fermentation on a chemically defined medium. Most often, carry-over from the inoculum will be detectable through the presence of a small amount of a complex nitrogen source in the chemically defined medium for the main fermentation.

In one embodiment, it can be advantageous to use a complex carbon and/or nitrogen source in the fermentation process of the inoculum for the main fermentation, for instance to speed up the formation of biomass, i.e. to increase the growth rate of the microorganism, and/or to facilitate internal pH control. For the same reason, it may be advantageous to add an essentially small amount of a complex carbon and/or nitrogen source, e.g. yeast extract, to the initial stage of the main fermentation, especially to speed up biomass formation in the early stage of the fermentation process.

An essentially small amount of a complex carbon and/or nitrogen source which may be present in the chemically defined medium of the invention is herein defined to be an amount of at the most about 10% of the total amount of carbon and/or nitrogen (Kjeldahl N) which is present in the chemically defined medium, preferably an amount of at the most 5, 2, 1, 0.5, 0.2 or 0.1% (w/v) of the total amount of carbon and/or nitrogen.

In a preferred embodiment, however, no complex carbon and/or nitrogen source is present in a chemically defined medium of the invention, other than the defoaming agent in as far as the defoaming agent can be used as a carbon source by the strain of a thermophilic fungus as cultured in a process of the invention. The fungal strains are preferably grown on a relatively pure carbohydrate (e.g. glucose) solution and ammonia in combination with a mineral salts solution (e.g. as described in US20140342396A1). The pure carbohydrate/sugar solutions allow the production with low levels of heavy metals, low toxic substances like herbicides, pesticides and fungicides, as well as low levels of mycotoxins derived from the feedstock, that may have been moulded during growth on the land, and or during storage and processing.

It is further to be understood that the term "chemically defined medium" as used herein, includes a medium wherein all necessary components are added to the medium before the start of the fermentation process, and further includes a medium wherein at least a part of the necessary components are added before starting and part are added or fed to the medium during the fermentation process.

A chemically defined medium to be used in the process of the invention typically contains so-called structural as well as so-called catalytic elements. Structural elements are understood as those elements which are constituents of microbial macromolecules, i.e. hydrogen, oxygen, carbon, nitrogen, phosphorus and sulphur. The structural elements hydrogen, oxygen, carbon and nitrogen typically are contained within the carbon and nitrogen sources. Phosphorus and sulphur typically are added as phosphate and sulphate and/or thiosulphate ions.

The type of carbon and nitrogen source which is used in the chemically defined medium is not critical to the invention, provided that the carbon and nitrogen source have essentially a chemically defined character.

In a preferred embodiment, the carbon source in the chemically defined medium is or consists of a hydrophilic carbon source such as e.g. a carbohydrate. The inventors have found that the problem with the fungal pellet morphology occurs when the fungus is grown at low pH in a chemically defined medium that lacks hydrophobic substances such as lipids (e.g. because the carbon source is hydrophilic) and that the desired dispersed morphology can be induced by including a small amount of hydrophobic substance, i.e. defoaming agent, in the medium. Thus, in its broadest sense, the invention pertain to a process for producing a fermentation product, wherein step a) of the process comprises growing a strain of a thermophilic fungus in a chemically defined medium, at a pH of less than 5.0, whereby the strain converts nutrients in the medium to the fermentation product and wherein the chemically defined medium comprises at least one hydrophobic compound or substance. Preferably the hydrophobic compound or substance is a defoaming agent as herein defined above. More specifically, in one embodiment, the strain of the thermophilic fungus is cultured in a chemically defined medium, consisting of a carbon source, a nitrogen source and further components necessary for growth of the fungus, wherein the carbon source in the chemically defined medium consist of at least one of a hydrophilic carbon source and the defoaming agent. The hydrophilic carbon source preferably comprises or consists of at least one of carbohydrate and organic acid. Preferably, the carbohydrate comprises a source of at least one of glucose, fructose, galactose, xylose, arabinose, rhamnose, fucose, galactose and mannose, of which glucose and fructose are preferred, and glucose is most preferred. Suitable carbohydrate carbon sources comprising a source of e.g. glucose and/or fructose include e.g. maltose, isomaltose, maltodextrins, starch, glucose syrups (e.g. corn syrups such as HCFS), inverted (cane or sugar beet) sucrose, a crude starch, a starch liquefact (e.g. by liquefying using alpha amylase such as Liquozyme (Novozymes) or Veretase (BASF), inulin, raffinose, melibiose and stachyose. Organic acids that can be comprised in the carbon source include lactic acid, acetic acid, galacturonic acid, glucuronic acid.

It is thus understood that the invention expressly includes that the defoaming agent is used as (at least part of) the carbon source, e.g. when the defoaming agent comprises an oil that can be utilised as carbon source by the fungal strain, such as a vegetable oil as mentioned above.

The nitrogen source in the chemically defined medium to be used in the processes of the invention preferably comprises or consists of at least one of urea, ammonia, nitrate, ammonium salts such as ammonium sulphate, ammonium phosphate and ammonium nitrate, and amino acids such as glutamate and lysine. More preferably, a nitrogen source is selected from the group consisting of ammonia, ammonium sulphate and ammonium phosphate. Most preferably, the nitrogen source is ammonia. The use of ammonia as a nitrogen source has the advantage that ammonia additionally can function as a pH-controlling agent. Preferably, when ammonia is used to control the pH, its concentration is controlled to be no more than 10, 20, 50, 100, 200, 500, 750 or 1000 mg/l. In case ammonium sulphate and/or ammonium phosphate are used as a nitrogen source, part or all of the sulphur- and/or phosphorus-requirements of the fungal strain may be met.

Catalytic elements are those elements which are constituents of enzymes or enzyme cofactors. These elements include e.g. magnesium, iron, copper, calcium, manganese, zinc, cobalt, molybdenum, selenium and borium. In addition to the aforementioned structural and catalytic elements, cations such as potassium and/or sodium preferably are present to function as a counter ion and for control of intracellular pH and osmolarity. Suitable mineral compositions for the chemically defined medium of the invention are described in US20140342396A1.

Compounds which may optionally be included in a chemically defined medium are chelating agents, such as citric acid, and buffering agents such as mono- and dipotassium phosphate, calcium carbonate, and the like. Buffering agents are preferably only added when dealing with processes without an external pH control.

Vitamins refer to a group of structurally unrelated organic compounds which may be necessary for the normal metabolism of thermophilic fungi. Fungi are known to vary widely in their ability or inability to synthesize the vitamins they require. A vitamin only needs to be added to the fermentation medium of a fungal strain incapable of synthesizing said vitamin. Typically, chemically defined fermentation media for lower fungi, e.g. Mucorales, may require supplementation with one or more vitamin(s). Higher fungi often have no vitamin requirement. Vitamins are selected from the group of thiamin, riboflavin, pyridoxal, nicotinic acid or nicotinamide, pantothenic acid, cyanocobalamin, folic acid, biotin, lipoic acid, purines, pyrimidines, inositol, choline and hemins.

In one embodiment, the thermophilic fungi that is grown in the process of the invention is a strain that does not require the presence of any vitamins in the chemically defined medium. The inventors have found that species of the genus *Rhizomucor*, e.g. the strains *Rhizomucor pusillus* CBS 143028, *Rhizomucor miehei* CBS 143029 and *Rhizopus* sp. CBS 143160, do not require any vitamins, even when grown on a mineral medium. In a preferred embodiment therefore, in step a) of the process the strain of the thermophilic fungus is a strain that does not require any vitamins and the strain is grown a chemically defined medium without any added vitamins, preferably on a chemically defined medium consisting of a carbon source as herein defined above, a nitrogen source as herein defined above and minerals, e.g. as described in US20140342396A1.

In one embodiment, the process of the invention is a batch process, more preferably at least step a) of the process is carried out as a batch process. In a preferred embodiment however, the process of the invention, or preferably at least step a) of the process, is carried out as is a fed-batch process, a repeated fed-batch process (wherein repeatedly a part of the fermentation broth is harvested) or a continuous process.

In a preferred embodiment, the process in step a) is a carbon-limited process, wherein preferably, the carbon source is fed at a growth-limiting rate by feeding continuously or by intermittent feeding. Preferably, in step a) of the process the dissolved oxygen concentration is maintained at a level of at least 0.1. 0.2, 0.5, 1.0, 2.0, 5.0 or 10 mg/l.

An advantage of the use of thermophilic fungi is that a fermenter can be operated without any cooling, e.g. without any (active) cooling device that requires an input of energy. Thus, neither an internal cooling coil in the fermenter nor cooling coil in baffles of a stirred fermenter, nor in fermenter wall, neither Riesel cooling is required, neither a cooling tower. An external cooling loop using a heat exchanger is not needed either. This will reduce the investment in the plant as the cooling relies only on evaporation of water and which will leave the fermenter via the exhaust gas exhaust of the fermenter via which the $CO_2$ is ventilated and/or heat that passively exchanged with the fermenter's environment. However, the invention does not exclude that the fermenter does need to be cooled to at least some extent, e.g. at higher growth rates.

Preferably, the fermenter has a means for introducing air, preferably sterile air (to prevent foreign fungal spores or yeasts to invade) and, preferably a means to control pH with e.g. $NH_3$ and/or $H_3PO_4$, $H_2SO_4$ or $H_2NO_3$. In some instances also a need for phosphate might be apparent and in such cases the use of ammonium phosphate is preferred in the processes of the invention.

The fermenter in which the processes of the invention are run can be in principle be any type of fermenter known in the art. The process can e.g. be carried in a fermenter comprising a bubble column (see e.g. van 't Riet and Tramper, 1991, Basic Bioreactor Design, Marcel Dekker Inc. ISBN 0-8247-8446-4, for description of types of bioreactors) or the fermenter can be a stirred tank fermenter. Advantageously the fermenter is a simple bubble column, which can be operated at very large scale such as e.g. >100 m$^3$, >200 m$^3$, >500 m$^3$, >1000 m$^3$, >2000 m$^3$ or >3000 m$^3$, thereby reducing the number of fermenters per factory, the total investment and operational cost. In this embodiment, the aeration is done to mix the broth, to (at least partly) cool the fermenter and also to provide oxygen for growth.

According to the invention the term "fermentation product" can be any substance derived from fermentation, i.e. a process including a fermentation step using a fermenting thermophilic fungus wherein a fungal strain of the invention is cultured in a medium comprising nutrients that are converted by the host cell into the fermentation product. The fermentation product can be, without limitation, an amino acid (e.g. aspartic acid, glutamic acid, glycine, lysine, serine, and threonine); an organic acid (e.g. acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a polyketide; antibiotics (e.g. penicillin); an enzyme; and hormones. Preferably however, the fermentation product is single cell protein in the form of biomass of thermophilic fungus.

Subsequent to fermentation the fermentation product may be separated from the fermentation medium and/or from the fungal cell. Methods for recovery of fermentation products are well known in the art.

In one embodiment, the process preferably comprises a further step of b) recovery of SCP from the medium in the form of biomass of the thermophilic fungus grown in step a). Preferably, the biomass is recovered from the medium by at least one of sieving, filtration and decantation. More preferably, the biomass is recovered from the medium by at least one of rotating drum filtration, a filter press, a belt filter, a decanter centrifuge and sieving. Preferably biomass is recovered by sieving on a sieve or a screen, preferably with 100 200, 300, 400 or 500 µm, or 0.6, 0.7, 0.8, 0.9, 1.0, 1.5, or 2 mm diameter of pores. The dispersed morphology of the fungus is also advantageous in this respect for having improved properties of good sieving/filtration and better compressibility of the biomass. More preferably, the biomass is recovered by at least two, three or four consecutive rounds of sieving on a sieve or screen whereby a smaller diameter of pores is applied in each subsequent round of sieving. E.g. a first round of sieving using 2 mm pore diameter, followed by subsequent rounds of 1, 0.5 and/or 0.1 mm.

In one embodiment, the biomass is subsequently washed pasteurized, preferably at a temperature of at least 60° C. Optionally, an antioxidant is added to the biomass before pasteurisation.

Optionally, dry matter concentration of the sieved, filtered or decanted biomass (cake) is further increased by further removal of water, i.e. drying. The biomass cake can e.g. be further dried by pressing (more of) the residual water out using e.g. compressed air using a pneumapress and/or mechanical pressing, using e.g. a belt press or a screw press, preferably to a dry matter concentration of at least 12, 15, 20, 25, 30, 35, 40, 45 or 50% (w/w). After pressing the biomass to a cake, optionally the cake can be milled or extruded e.g. to enable drying, preferably air drying. Preferably, the particle size of the pressed mycelial biomass cake is reduced by physical means to enable (more efficient) drying of the pressed cake. This can optionally done by extrusion of the mycelial cake through holes with a diameter of 0.6, 0.7, 0.8, 0.9, 1.0, 1.2, 1.4, 1.6, 1.8 or 2 mm, using extruders that are known in the art per se. If however the dry matter concentration of the pressed cake after pressing is so high, that extrusion of the pressed cake is no longer possible (e.g. when the cake is too firm to allow for extrusion), the particle size of the cake can be reduced by a combination of milling and sieving. As a milling step any type of mill known in the art per se can be used, such as e.g. a knife mill or a hammer mill, etc. To obtain homogeneous particle size of the milled pressed cake, the larger particles still present after milling can be removed before drying by sieving with a pore diameter size in the sieve of 0.5, 1.0, 1.2, 1.4, 1.6, 1.8, 2.0, 2.5 or 3 mm. The resulting milled cake would have preferably a particle size between 1-3 mm before drying. By reducing the particle size, evaporation of water from the pressed cake is more efficient and faster.

Preferably drying of the cake is done by using waste heat, e.g. from a plant where hot water is obtained after condensation of gas (e.g. ethanol distillation, potato cooking, steam-pealing of potatoes, etc.). The air can be heated using a heat exchanger to heat up dry air with hot water from the heat source.

Drying of the extruded or milled cake is preferably done at temperatures of 30-70° C. The hot air can then dry the cake in a gentle and cost effective way in a belt dryer or fluid bed dryer. Steam drying at high temperatures (e.g. >80° C.) is not preferably avoided as it can negatively influence digestibility of the proteins by denaturing and baking and even chemical decomposition of the amino acids by Maillard reactions. Alternatively, the extruded or milled cake is dried under vacuum in freeze drying process or by flash drying.

In a second aspect the invention relates to an SCP product comprising biomass of a thermophilic fungal strain as herein defined above. Preferably, the biomass is obtainable or produced in a process as herein described above. Preferably, the biomass comprises at least 1, 2, 5, 10, 25, 50, 75, 100, 125 or 135 ppm (w/v) of a defoaming agent as herein defined above. Preferably, the SCP product comprises or consists of pressed or dried biomass with a dry matter concentration of at least 12%, 15%, 20%, 25%, 30%, 35%, 40%, 45%, 50%, 52%, 53% 54% or 55% (w/v) and which optionally is milled or extruded to an average particle size in the range of 1-3 mm. With this the product can be conveyed to pack it, convey it to a next processing step. The protein rich product can then subsequently be further dried to a water content of no more 10%, 5%, 2%, 1%, 0.5%, 0.2%, 0.1% (w/w). The SCP product can thus be biomass, a biomass cake or a biomass powder, recovered, pressed, dried, milled and/or extruded as described hereinabove.

In a third aspect the invention relates to food or beverage product, a pet food product or animal feed comprising an SCP product as herein defined above.

In a fourth aspect the invention pertains to the use of a defoaming agent as defined above herein for at least one of i) preventing pellet morphology; ii) inducing dispersed morphology; and iii) maintaining dispersed morphology, of a strain of thermophilic fungus as defined above herein, when grown at acidic pH as defined above herein in a chemically defined medium as defined above herein.

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1

Difference in growth morphology of *Rhizomucor pusillus*. 25 ml of culture broth in displayed in plates after 19 hours of growth in 200 ml media in shake flasks at 46° C., in an orbital shaker at 200 rpm. From left to right with increasing amount of olive oil as indicated: 0, 25, 50, 100, 143 ppm. Upper and lower rows represent duplicates.

EXAMPLES

Example 1

Growing *Rhizomucor pusillus* at Low pH with Varying Carbon Sources

For preculture of *Rhizomucor pusillus* strain CBS 143028, the strain is inoculated in 35 ml of a preculture medium pH 5.5 containing the defined mineral medium containing KCl 0.17 gr/L, $KH_2PO_4$ 1.3, $Na_2HPO_4$ 0.4, Citric acid 0.5 gr/L, $MgSO_4 \cdot 7$ aq 0.7 gr/L, $FeSO_4 \cdot 7$ aq 0.03 gr/L, $CaCl_2 \cdot 2$ aq 0,035 gr/L, $ZnSO_4 \cdot 7$ aq 0.04 gr/L, $MnCl_2 \cdot 4$ aq 0,004, $CuSO_4 \cdot 5$ aq 0,0005 gr/L, $CoCl_2 \cdot 6$ aq 0,0005 gr/L, $Na2B_4O_7 \cdot 10$ aq 0,003 gr/L, KI 0,0003 gr/L, $Na_2MoO_4 \cdot 2$ aq 0,0005 gr/L, 11 g Dextrose per l; 4 g $(NI-14)_2SO_4$ per l; and 7.5 g tartaric acid per l. The culture is incubated for 24 hours at 46° C., in a 250 ml Erlenmeyer flask with air permeable stop with baffles, in an orbital shaker at 200 rpm. Under these conditions (pH 5.5, pure dextrose as carbon source) the strain grew well with a dispersed morphology.

Next 1 ml of the above preculture was used to inoculate 35 ml of a pH 3.5 medium containing a complex carbon source: 400 g potato liquefact per l (peeled potatoes were mashed at 7.5% dry matter and liquefied using Veretase™ of BASF at 95 C, 60 minutes, pH 4.5). The medium further contained 4 g $(NH_4)_2SO_4$ per l; 7.5 g tartaric acid per l, per l, 1.6 g $(NH_4)_2PO_4$ per l, $ZnSO_4 \cdot 7$ aq 0.05 gr/L. The incubation is continued for 24 hours at 46° C. in a 250 ml baffled Erlenmeyer flask with air permeable stop. Under these conditions (pH 3.5, complex carbon source) the strain grew well with a dispersed morphology.

In parallel, 1 ml of the above preculture was used to inoculate 35 ml of pH 3.5 medium containing: KCl 0.5 gr/L; $KH_2PO_4$ 4, $Na_2HPO_4$ 1.1, Citric acid 1.5 gr/L, $MgSO_4 \cdot 7$ aq 2 gr/L, $FeSO_4 \cdot 7$ aq 0.1 gr/L, $CaCl_2 \cdot 2$ aq 0.1 gr/L, $ZnSO_4 \cdot 7$ aq 0,125 gr/L, $MnCl_2 \cdot 4$ aq 0,012, $CuSO_4 \cdot 5$ aq 0,00016 gr/L, $CoCl_2 \cdot 6$ aq 0,00015 gr/L, $Na2B_4O_7 \cdot 10$ aq 0,0009 gr/L KI 0,00009 gr/L, $Na_2MoO_4 \cdot 2$ aq 0,00015 gr/L 22 g Dextrose per l; 4 g $(NH_4)_2SO_4$ per l; 7.5 g tartaric acid per l. The incubation is continued for 24 hours at 46° C. in a 250 ml baffled Erlenmeyer flask with air permeable stop. Under these conditions (pH 3.5, pure dextrose as carbon source) the strain grew with a pellet morphology and growth appeared to have slowed down.

Thus, we observed that while the *Rhizomucor* fungus grows well in a dispersed morphology on a complex carbon source at low pH (i.e. pH 3.5) and on a chemically defined medium (with dextrose as C-source) at higher pH (i.e. pH 5.5), the combination of a low pH and a chemically defined medium with dextrose as C-source reduced growth of the fungus, which was observed to no longer grow in a dispersed morphology but to form pellets. We next set out to address this issue.

*Rhizomucor pusillus* strain CBS 143028 is inoculated in 200 ml of a preculture medium at pH 5.5 containing a defined mineral composition containing KCl 0.5 gr/L; $KH_2PO_4$ 4, $Na_2HPO_4$ 1.1, Citric acid 1.5 gr/L, $MgSO_4 \cdot 7$ aq 2 gr/L, $FeSO_4 \cdot 7$ aq 0.1 gr/L, $CaCl_2 \cdot 2$ aq 0.1 gr/L, $ZnSO_4 \cdot 7$ aq 0.125 gr/L, $MnCl_2 \cdot 4$ aq 0.012, $CuSO_4 \cdot 5$ aq 0.0016 gr/L, $CoCl_2 \cdot 6$ aq 0.0015 gr/L, $Na2B_4O_7 \cdot 10$ aq 0.009 gr/L KI 0.0009 gr/L, $Na_2MoO_4 \cdot 2$ aq 0.0015 gr/L; 11 g Dextrose per l as C-source; 4 g $(NH_4)_2SO_4$ per l as N-source; and 7.5 g tartaric acid per l. The culture is incubated for 24 hours at 46° C., in a 1 l Erlenmeyer flask with air permeable stop with baffles, in an orbital shaker at 200 rpm.

1 ml of the preculture is then used to inoculate 35 ml of pH 3.5 medium containing a defined mineral medium as described above comprising 22 g Dextrose per l as C-source; 4 g $(NH_4)_2SO_4$ per l as N-source; 7.5 g tartaric acid per l; and 1.2 g sunflower oil per l.

The incubation is continued for 96 hours in a 250 ml baffled Erlenmeyer flask with air permeable stop. At the end of fermentation the packed mycelial volume (PMVV) is determined by centrifugation (15 min×g) and growth morphology is judged by eye. Morphology was ranked 1 on a 1 to 5 scale for pellet formation (1 being dispersed and 5 being only round pellets). When sunflower oil was added to the medium the fungus grew well with a dispersed morphology. This can also explain why the fungus grows well and in a dispersed morphology when using a potato liquefact as carbon source because potato is known to contain a small amount (±100 ppm of lipids).

Example 2

Growing *Rhizomucor pusillus* with or without Oil

*Rhizomucor pusillus* strain CBS 143028 is inoculated in 200 ml of a preculture medium at pH 5.5 containing a defined mineral medium as described above comprising 22 g Dextrose per l as C-source; 4 g $(NH_4)_2SO_4$ per l as N-source; and 7.5 g tartaric acid per l. The culture is incubated for 24 hours at 46° C., in a 1 l Erlenmeyer flask with air permeable stop with baffles, in an orbital shaker at 200 rpm.

1 ml of the preculture is then used to inoculate 35 ml of pH 3.5 medium containing a defined mineral medium as described above comprising 22 g Dextrose per l as C-source; 4 g $(NH_4)_2SO_4$ per l as N-source; 7.5 g tartaric acid per l; and with or without 0.14 g olive oil per l.

The incubation is continued for 24 hours in a 250 ml baffled Erlenmeyer flask with air permeable stop. At the end of fermentation the glucose concentration is determined by a biochemistry analyser and growth morphology is judged by eye. The addition of olive oil resulted in a 2 times faster consumption of glucose and the morphology was observed to be dispersed in contrast to the pellets in the negative control.

Example 3

Growing *Rhizomucor pusillus* with Varying Antifoaming Agents

*Rhizomucor pusillus* strain CBS 143028 is inoculated in 200 ml of a preculture medium at pH 5.5 as described in Example 2. The culture is incubated for 24 hours at 46° C., in a 1 l Erlenmeyer flask with air permeable stop with baffles, in an orbital shaker at 200 rpm.

1 ml of the preculture is then used to inoculate 35 ml of pH 3.5 medium as described in Example 2, with or without either 0.14 g olive oil per l, 0.14 g polypropylene glycol (PPG) per l or 0.14 g Antifoam C100K per l (KCC Basildon Chem. Comp. Ltd, Abingdon, Oxford, UK).

The incubation is continued for 19 hours in a 250 ml baffled Erlenmeyer flask. At the end of fermentation the glucose concentration is determined by a biochemistry analyser, pH was determined and growth morphology is judged by eye. The results are summarized in Table 1.

TABLE 1

Residual glucose and pH after 19 hours incubation of *Rhizomucor pusillus*. Incubation conditions; 35 ml, 200 rpm, 46° C., start pH 3.5. Error bars are the result of duplicates.

| defoamer | glucose (g/l) | PH |
|---|---|---|
| None | 18.1 ± 2.2 | 3.4 ± 0.1 |
| Olive oil | 5.9 ± 4.2 | 2.9 ± 0.1 |
| C100K | 6.5 ± 2.2 | 2.9 ± 0.1 |
| PPG | 6.9 ± 1.8 | 2.9 ± 0.1 |

The addition of antifoaming agent PPG resulted in a 6.9 times higher consumption of glucose, and C100K resulted in a 6.7 times higher consumption of glucose. With both defoaming agents the morphology was observed to be dispersed contrary to the pellets in the negative control without defoaming agent.

Example 4

Growing a Thermophilic Fungus at Different Concentrations of Antifoaming Agent

The above experiments showed that the addition of 143 ppm olive or sunflower oil had a positive effect on the dispersed growth morphology of *Rhizomucor pusillus* at low pH. We next set out to determine whether this effect is also seen at lower concentrations of the antifoaming agent.

A concentration range from 143 till 25 pmm olive oil was tested in shake flasks under conditions essentially as described in Examples 2 and 3, except that the fungus was grown in 200 ml medium. As olive oil cannot be diluted in aqueous media the lower limit in this experiment is 25 ppm. The flasks were filled with standard media and brought to pH 3.5, sterilized and inoculated with 3% preculture (same media pH 5.5). After 19 hours the different flasks were judged on morphology, glucose concentration and pH were measured. The glucose concentration (starting at 20 g/l) and pH are indicators for growth, as *Rhizomucor pusillus* consumes the buffer and thereby lowering the pH. Experimental results presented in Table 1 are the product of duplicates.

TABLE 2

Residual glucose and pH after 19 hours incubation of *Rhizomucor pusillus*. Incubation conditions; 200 ml, 200 rpm, 46° C., start pH 3.5. Error bars are the result of duplicates.

| Olive oil ppm | glucose (g/l) | PH |
|---|---|---|
| 0 | 18 ± 0.6 | 3.5 ± 0.1 |
| 25 | 11.05 ± 0.2 | 3.1 ± 0.0 |
| 50 | 10.45 ± 0.4 | 3.1 ± 0.0 |
| 100 | 12.45 ± 0.5 | 3.2 ± 0.0 |
| 143 | 13.15 ± 1.2 | 3.2 ± 0.0 |

We conclude from Table 2 that the growth of the negative control was more than 4 times slower than ones with the addition of olive oil, even at the lowest concentration tested in this experiment. As 25 ppm was the lowest concentration of olive oil that could reliably be diluted at this scale, we expect that even lower concentration of olive oil, e.g. 10, 5 or even 1 ppm still produce the advantageous effects. The measurements in Table 2 are consistent with the observations by eye as shown in FIG. 1.

Example 5

Growing a Thermophilic Fungus in a Fermenter with Olive Oil as Anti-Foaming Agent For preculture *Rhizomucor pusillus* strain CBS 143028 was inoculated in 200 ml of a defined mineral medium at pH 5.5 containing KCl 0.17 g/L, $KH_2PO_4$ 1.3 g/L, $Na_2HPO_4$ 0.4 g/L, citric acid 0.5 gr/L, $MgSO_4 \cdot 7$ aq 0.7 gr/L, $FeSO_4 \cdot 7$ aq 0.03 gr/L, $CaCl_2 \cdot 2$ aq 0.035 gr/L, $ZnSO_4 \cdot 7$ aq 0.04 gr/L, $MnCl_2 \cdot 4$ aq 0.004, $CuSO_4 \cdot 5$ aq 0.0005 gr/L, KI 0.0003 gr/L, 22 g Dextrose per L; 4 g $(NH_4)_2SO_4$ per L; and 7.5 g tartaric acid per L. The preculture was incubated for 24 hours at 46° C., in a 1 L Erlenmeyer flask with air permeable stop with baffles, in an orbital shaker at 200 rpm. The preculture was then used to inoculate a fermenter with 11 L working volume containing the defined mineral medium as described above at a pH of 3.5 and comprising 77 g Dextrose per L as C-source; 1.4 g $(NH_4)_2SO_4$ per L as N-source and supplemented with $NH_3$ as titrant. The fungus was grown in the fermenter in batch mode for 24 hours. Olive oil was continuously being fed to maintain a concentration of 50 ppm. At the end of the batch, the growth of the fungus was still dispersed and no pellets were formed.

Example 6

Growing a Thermophilic Fungus in a Fermenter with Anti-Foaming Agent Struktol SB 420

For preculture *Rhizomucor pusillus* strain CBS 143028 was inoculated in 200 ml of a defined mineral medium at pH 5.5 containing KCl 0.17 gr/L, $KH_2PO_4$ 1.3 gr/L, $Na_2HPO_4$ 0.4 gr/L, citric acid 0.5 gr/L, $MgSO_4 \cdot 7$ aq 0.7 gr/L, $FeSO_4 \cdot 7$ aq 0.03 gr/L, $CaCl_2 \cdot 2$ aq 0.035 gr/L, $ZnSO_4 \cdot 7$ aq 0.04 gr/L, $MnCl_2 \cdot 4$ aq 0.004, $CuSO_4 \cdot 5$ aq 0.0005 gr/L, KI 0.0003 gr/L, 22 g Dextrose per L; 4 g $(NH_4)_2SO_4$ per L; and 7.5 g tartaric acid per L. The preculture was incubated for 24 hours at 46° C., in a 1 L Erlenmeyer flask with air permeable stop with baffles, in an orbital shaker at 200 rpm. The preculture was then used to inoculate a fermenter with 8 L working volume containing mineral medium at a pH of 3.5 containing $KH_2PO_4$ 2.7 gr/L, $MgSO_4 \cdot 7$ aq 1.3 gr/L, $CaCl_2 \cdot 2$ aq 0.067 gr/L, KCl 0.33 gr/L, $Na_2HPO_4$ 0.73 gr/L, $FeSO_4 \cdot 7$ aq 0.07 gr/L, $ZnSO_4 \cdot 7$ aq 0.08 gr/L, $MnCl_2 \cdot 4$ aq 0.008, KI 0.0006 gr/L and comprising 5.5 g Dextrose per L as C-source; 0.8 g Urea per L as N-source. The fungus was grown in the fermenter in batch mode for 18 hours. Struktol SB 420 (www.struktol.de) was added to a final concentration of 0.2 gr/L. At the end of the batch, the growth of the fungus was still dispersed and no pellets were formed.

The invention claimed is:

1. A process for producing a fermentation product, wherein the process comprises the steps of:
   a) growing a strain of a thermophilic fungus in submerged culture in a chemically defined medium comprising a carbon source, a nitrogen source and minerals, at a pH of less than 5.0, whereby the strain converts at least one of the carbon and nitrogen sources in the medium to the fermentation product, and wherein the strain is cultured in the presence of a food-grade defoaming agent to maintain a dispersed morphology of the strain; and, b) optionally, recovery of the fermentation product produced in step a), wherein the carbon source consists of at least one of a hydrophilic carbon source and the food-grade defoaming, agent and the nitrogen source consists of at least one of urea, ammonia, nitrate and ammonium salts, and wherein the fungal strain is a strain of a fungal genus *Rhizomucor*.

2. The process according to claim 1, wherein the defoaming agent is at least one of an oil-based defoamer, a polyalkylene glycol-based defoamer and a silicon-based defoamer.

3. The process according to claim 1, wherein the defoaming agent comprises a vegetable oil.

4. The process according to claim 1, wherein the defoaming agent is present and maintained in the chemically defined medium at a concentration of at least 25 ppm (w/v).

5. The process according to claim 1, wherein the fungal strain is of the species *Rhizomucor pusillus*.

6. The process according to claim 1, wherein the hydrophilic carbon source consists of at least one of a carbohydrate and an organic acid.

7. The process according to claim 1, wherein no vitamins are added to the medium.

8. The process according to claim 1, wherein step a) of the process, is carried out as is a fed-batch process, a repeated fed-batch process or a continuous process.

9. The process according to claim 1, wherein the fermentation product is single cell protein in the form of biomass of thermophilic fungus, wherein the process optionally comprises a step b) of recovery of SCP from the medium in the form of biomass of the thermophilic fungus grown in step a).

10. The process according to claim 9, wherein the biomass is recovered from the medium by at least one of sieving, filtration and decantation.

11. The process according to claim 10, wherein the biomass is milled and further dried to a biomass powder by warm air, by freeze drying, or by flash drying to a water content of no more than 5% (w/w).

12. The process according to claim 3, wherein the vegetable oil is selected from the group consisting of canola (rapeseed) oil, coconut oil, corn oil, cottonseed oil, olive oil, palm oil, palm kernel oil, linseed oil, peanut oil, safflower oil, soya bean oil, sunflower oil and high-oleic sunflower oil.

13. The process according to claim 5, wherein the strain is *Rhizomucor pusillus* strain CBS 143028b1945.

* * * * *